United States Patent [19]
Risteli et al.

[11] Patent Number: 5,698,407
[45] Date of Patent: Dec. 16, 1997

[54] METHOD FOR THE IMMUNOLOGICAL DETERMINATION OF THE CARBOXYTERMINAL PROPEPTIDE OF TYPE I PROCOLLAGEN

[75] Inventors: Juha Risteli; Leila Risteli; Jukka Melkko, all of Oulu, Finland

[73] Assignee: Orion-Yhtyma OY, Espoo, Finland

[21] Appl. No.: 464,557

[22] Filed: Jun. 5, 1995

Related U.S. Application Data

[63] Continuation of Ser. No. 345,352, Nov. 18, 1994, abandoned, which is a continuation of Ser. No. 999,187, Dec. 30, 1992, abandoned, which is a continuation of Ser. No. 718,176, Jun. 20, 1991, abandoned.

[30] Foreign Application Priority Data

Jun. 26, 1990 [GB] United Kingdom ............... 9014220

[51] Int. Cl.$^6$ ................................................ G01N 33/53
[52] U.S. Cl. ........................ 435/7.9; 435/7.92; 435/7.93; 435/7.94; 435/971; 435/975; 436/536; 436/538; 436/540; 436/804; 436/805; 436/808; 530/387.1; 530/388.1; 530/389.1; 530/391.1; 530/391.3
[58] Field of Search ........................ 435/7.9, 7.92, 435/7.93, 7.94, 971, 975; 436/518, 536, 538, 540, 542, 804, 805, 808, 387.1; 530/388.1, 389.1, 391.1, 391.3

[56] References Cited

FOREIGN PATENT DOCUMENTS 2 208 865  4/1989  United Kingdom .
89/10177  11/1989  WIPO .

OTHER PUBLICATIONS

Taubman et al., "Radioimmunoassay of Procollagen in Serum of Patients with Paget's Disease of Bone", *Proc. Soc. Exp. Biol. Med.*, vol. 152, pp. 284–287 (1976).

Melkko et al., "Radioimmunoassay of the Carboxy Terminal Propeptide of Human Type I Procollagen", *Clin. Chem.*, vol. 36, No. 7, pp. 1328–1332, (1990).

Simon et al., *J. Clin. Endocrin Metab.*, vol. 58, No. 1, pp. 110–120, (1984).

McDonald et al., *J. Clin. Invest.*, vol. 78, pp. 1237–1244, (1986).

Malizia, et al., *The Lancetti*, pp. 1055–1057, (1987).

Oellerich, *J. Clin Chem Clin Biochem*, vol. 22, pp. 895–904, (1984).

B.R. Olsen et al, *Biochemistry*, vol. 16, No. 13, Jun. 28, 1977, pp. 3030–3036.

K.P. Mintz et al, Chemical Abstracts, vol. 113, No. 17, Oct. 22, 1990 p. 379, Abs. No. 148293v, Columbus, Ohio, U.S.

M. Katayama et al, Chemical Abstracts, vol. 113, No. 17, Oct. 22, 1990 p. 378, Abs. No. 148282a, Columbus, Ohio, U.S.

Y. Niitsu et al, Chemical Abstracts, vol. 109, No. 17, Oct. 24, 1988 p. 522, Abs. No. 147210w, Columbus, Ohio, U.S.

B.H. Davis et al, Chemical Abstracts, vol. 106, No. 19, May 11, 1987 p. 349, Abs. No. 152462x, Columbus, Ohio, U.S.

J.A. McDonald et al, Chemical Abstracts, vol. 105, No. 25, Dec. 22, 1986, Abs. No. 223803b, Columbus, Ohio, U.S.

E. Kessler et al, Biological Abstracts, vol. 89, No. 5, 1990, p. 553, Abs. No. 45366, Philadelphia, PA, U.S.

G. Malizia et al, Biological Abstracts, vol. 85, No. 4, 1988 p. 349, Abs. No. 35511, Philadelphia, PA, U.S.

L. Risteli, Scand J Clin Invest, vol. 50, Supplement 202, 1990, pp. 143–146.

J. Melkko et al, Clinical Chemistry vol. 36, No. 7, Jul. 1990, pp. 1328–1332, Washington, D.C., U.S.

Goldberg et al., "The Carboxyl Fragment Released by Bacterial Collagenase From Human Type I Procollagen: Antibodies to the Peptide Determinants", *Collagen Rel. Res.*, vol. 5, 1985, pp. 393–404.

Risteli et al., "The Carboxyterminal Propeptide of Procollagen Type I (PICP) In Serum and Biological Fluids", *Abstract of paper given at the XXII Nordic Congress of Clinical Chemistry* (Jun. 25 to 28, 1990).

*Primary Examiner*—James C. Housel
*Assistant Examiner*—Susan Wolski
*Attorney, Agent, or Firm*—Adduci, Mastriani & Schaumberg, LLP

[57] ABSTRACT

A carboxyterminal propeptide of type I procollagen free from type III procollagen carboxyterminal propeptide can be used to produce an antibody which is specific for carboxyterminal propeptide of type I procollagen and which has no affinity for the type III procollagen carboxyterminal propeptide. This antibody can be used to assay more accurately the propeptide which is a measure of the rate of production of type I procollagen and useful in diagnosing and monitoring e.g. bone diseases.

8 Claims, 1 Drawing Sheet

METHOD FOR THE IMMUNOLOGICAL DETERMINATION OF THE CARBOXYTERMINAL PROPEPTIDE OF TYPE I PROCOLLAGEN

This application is a continuation of application Ser. No. 08/345,352, filed Nov. 18, 1994, now abandoned, which is a continuation of application Ser. No. 07/999,187, filed Dec. 30, 1992, now abandoned, which is a continuation of application Ser. No. 07/718,176, filed Jun. 20, 1991, now abandoned.

The present invention relates to a method of measuring type I procollagen synthesis in humans.

Type I collagen is found in several different types of connective tissues throughout the human body, but most of it is present in bones, where it forms more than 95% of the organic matrix. Many diseases are associated with an increase in the amount of collagen synthesized i.e. an increase in the rate of bone matrix formation and turnover. In particular it would be desirable to be able to assess this rate since osteoporosis and other metabolic bone diseases are a common health problem and such assessment would provide guidance in formulating a therapy for these disorders.

Type I collagen is synthesized as a procollagen containing propspride extensions at both ends of the molecule. The rate of type I collagen synthesis can thus be assessed by determining the amount of propspride liberated during the conversion of the procollagen to the collagen. An assay for a propspride of type I procollagen has been described (Taubman et al., Science 186, 1115–1117, 1974) and refers to an antigen which was believed to be the aminoterminal propeptide of type I procollagen. However, the antigen measured was later shown to be most likely derived from the carboxyterminal portion.

Moreover, the propeptide antigen used in this assay, having been purified from procollagen produced by cultured fibroblasts, has been shown to react also with the corresponding propeptide of type III procollagen (Simon et al., J. Clin. Endocrinol. Metab. 58, 110–120, 1984). When the propeptide antigen is reduced and then studied in SDS-polyacrylamide gel electrophoresis three to four different bands result (Goldberg et al., Collagen Rel. Res. 5, 393–404, 1985; FIG. 3 on page 398). This is consistent with the extra presence of chains derived from carboxypropeptide of type III procollagen. Thus the assay described previously is not specific for type I procollagen.

Cultured human skin fibroblasts always produce both type I and III procollagens. However, it is technically difficult to completely separate the two types from each other. Salt fractionation, the most commonly used separation method, does not result in complete separation. The concentration of type III procollagen is often monitored using an assay for the aminoterminal propeptide of type III procollagen. However, this is not sufficiently sensitive since it does not recognize molecules that contain the carboxyterminal propeptide but have lost the aminoterminal one (such molecules are known as type III pC-collagen).

The present invention, therefore seeks to develop a method for producing the carboxyterminal propeptide of type I procollagen (abbreviated PICP), free from the corresponding propeptide of type III procollagen (abbreviated PIIICP), and to create a quantitative method, which is quick and simple to practice, for assessing the quantity of carboxyterminal propeptide of type I procollagen in human serum.

The present invention provides carboxyterminal propeptide of type I procollagen, free from propeptide of type III procollagen.

The preparation of the purified propeptide starts from a material containing a sufficient concentration of either the free propeptide or type I procollagen. Examples of the former include e.g. ascitic fluid, interstitial fluid of a healing wound and serum. Cell culture medium of human fibroblasts is an example of the latter. However, cultured human fibroblasts differ in their suitability for producing procollagen starting material. Primary cultures kept in the presence of relatively high concentrations of calf serum (higher than 10%) produce the highest amounts of procollagen. These are of course only examples other sources can be used as well.

If starting from the procollagen source it is convenient to remove a portion, more conveniently most, of type III procollagen from type I procollagen at the procollagen stage e.g. to remove at least 80% preferably at least 90%, more preferably at least 95% by weight of the type III procollagen based on the total weight of type III procollagen present. This may be done by a series of precipitations e.g. using ammonium sulphate and sodium chloride. This is followed by gel filtration and ion exchange chromatographies.

Final separation of PICP from PIIICP is obtained at the propeptide stage. Transformation of the procollagens to the propeptide may be achieved by e.g. bacterial collagenase digestion of the procollagens. The PICP may then purified by lectin binding, gel filtration and chromatography.

Both PICP and PIIICP contain mannose-rich oligosaccharide side chains and they thus bind to concanavalin A lectin. The efficient separation of PICP from the contaminating PIIICP is then based on the fact that the latter, when produced by cultured human fibroblasts, is phosphorylated and thus, because of its more negative charge, is eluted much later than PICP during chromatography. It is preferred that the chromatography is carried out using ion exchange chromatography and reverse phase chromatography at pH above 4.0. The NaCl gradient of e.g. a DEAE-SEPHACEL ion-exchange chromatography column differentially elutes the PIIICP and PICP.

The desalting of the preparation and the final purification of the PICP may be achieved by reverse phase chromatography. The chromatographies should be performed under conditions such that the propeptide is not denatured. It is preferred that the above chromatographies are carried out in such conditions that the pH of the preparation stays between 4.0–8.5. It is known that handling of procollagens and propeptides is difficult in practice, leading to low yields. Detailed conditions for a typical purification procedure by which PICP can be isolated essentially free from PIIICP are given in the Example which follows.

When starting from a mixture of propeptides (type I and type III), the type I propeptide may be obtained by gel filtration e.g. on SEPHACRYL S-300, lectin affinity binding e.g. using concanavalin A lectin, ion exchange chromatography e.g. on DEAE cellulose and reverse phase chromatography above pH 4.0.

The isolated propeptide is homogeneous on SDS-polyacryl-amide gel electrophoresis. Upon reduction the electrophoresis, in contrast to previous preparations, produces only two bands, with approximate molecular masses of around 30,000 and with an approximate ratio of 2:1. This indicates that propeptide of type III procollagen is absent. Aminoterminal sequence analysis also confirms that no chains derived from carboxyterminal propeptide of type III procollagen are present.

The invention also provides an antibody, raised against the carboxyterminal propeptide of type I procollagen, particularly an antibody which has no affinity for the carboxyterminal propeptide of type III procollagen. The antibody may be monoclonal or polyclonal, preferably monoclonal, and may be of IgG or IgM-type. The antibody may be raised using techniques known in the art. For example immunization with the propeptide can be carried out as described for another procollagen propeptide antigen in Niemela O, Risteli L, Parkkinen J & Risteli J, Biochem. J. 232, 145–150, 1985.

The present invention also provides a method for assaying carboxyterminal propeptide of type I collagen, which comprises contacting in any order (i) a sample which is known or suspected to contain the propeptide; (ii) an antibody of the invention, and (iii) a label, such that the label is bound in an amount which depends on the amount of propeptide present in the sample, and assaying the amount of bound and/or unbound label as a measure of the presence or level of carboxyterminal propeptide of type I procollagen in the sample.

The new assay ensures rapid and accurate analysis of the propeptide concentration. It is especially useful in those clinical conditions where the actual changes in concentration between successive assays are not very large. Examples of this are the effect of estrogen treatment in osteoporotic patients and growth hormone treatment in growth hormone deficient children.

The assay may be carried out by contacting the antibody to the propeptide, the first antibody, in the presence of a label, with carboxyterminal propeptide of type I procollagen and the sample to be assayed, separating the labelled propeptide-antibody complex so formed from the uncomplexed material and assaying the complexed and/or uncomplexed label. The complex formed from the propeptide and the antibody, the first antibody, may be contacted with a second antibody which is an antibody to the first antibody and which may be bound to a solid support. The propeptide-antibody-antibody complex may then be separated from the uncomplexed material.

If carboxyterminal propeptide of type I procollagen is used in the assay as an index antigen it must be free from carboxyterminal propeptide of type III procollagen (PIIICP).

This immunological assay of the propeptide, using the reagents prepared in the way described, may be carried out e.g. with a radioactive, fluorescent, luminescent or enzymic label either in the index antigen or in the antibody. Conveniently the label is attached to the index antigen, purified carboxyterminal propeptide of type I procollagen. Either polyclonal or monoclonal antibodies can be used. In adults the concentration of the propeptide is normally about 40 to 200 micrograms/liter serum. In infants and children the concentration is significantly higher.

The present invention also provides a kit suitable for carrying out the assay method. The kit may comprise an antibody specific to carboxyterminal propeptide of type I procollagen and a label. If the assay method involves contacting a complex formed from the propeptide and the first antibody with a second antibody, and separating out complexed and uncomplexed material then the assay kit suitably comprises a first antibody which is specific to carboxyterminal propeptide of type I procollagen, a second antibody which is an antibody to the first antibody, a label and a solid support to which is bound the first or second antibody.

The following examples illustrate the invention. In Example 1 culture medium from human fibroblasts was used. However, it is also possible to use cells and fluids from other species, such as bovine, ovine and porcine to obtain antibodies that show sufficient cross-reaction with the human PICP.

EXAMPLE 1

Isolation of the carboxyterminal propeptide of human type I procollagen free from carboxyterminal propeptide of type III procollagen.

30 liters of culture medium of human skin fibroblasts are precipitated with solid $(NH_4)_2SO_4$ (20% saturation). The precipitated proteins are collected by centrifugation at 15,000×g for 30 min, dissolved in and dialyzed against 50 mM Tris/HCl, pH 7.4, 1M NaCl containing protease inhibitors (3 milligrams/liter of phenylmethylsulfonyl fluoride, N-ethyl-maleimide and p-hydroxymercuribenzoate and 10 mM EDTA) and precipitated with solid NaCl (final concentration 1.7M). The supernatant, containing most of the type I procollagen, is chromatographed on a column of SEPHACRYL S-500, and the fractions corresponding to procollagens are pooled and dialyzed against DEAE starting buffer (see below). The sample is then chromatographed on a DEAE-SEPHACEL column (5×30 cm) equilibrated in 50 mM Tris/HCl, pH 8.0, 6M urea containing the protease inhibitors as above. Elution is carried out with a linear gradient of NaCl; (0–0.3M NaCl; 3000+3000 ml). The fractions containing type I procollagen are pooled, dialyzed against 50 mN Tris/HCl buffer containing 0.5m NaCl and the protease inhibitors mentioned above. The procollagen preparation is then passed over a column (2×20 cm) of Con-A SEPHAROSE (Pharmacia, Uppsala, Sweden) and after binding to the column eluted with 0.5M alfa-methylmannoside. After dialysis against 0.2M $NH_4HCO_3$ the preparation is lyophilized. The isolated procollagen, which still contains traces of type III procollagen as judged by an assay for the aminoterminal propeptide of type III procollagen, is digested for 15 hours at +30° C. with highly purified bacterial collagenase (Worthington, grade CLSPA), using 9 mg of enzyme/30 L original medium volume. After gel filtration on SEPHACRYL S-300 (2.5×120 cm in 0.2M $NH_4HCO_3$) and lyophilization the propeptide preparation is dialyzed against 50 mM Tris/acetate buffer pH 8.6 and chromatographed using an HPLC instrument on a Protein Pak DEAE 5PV column (waters, Milford, Mass., USA) and eluting the bound propeptide with a linear gradient of NaCl (0–60 min, 0–0.5M). Final purification is achieved by the pH stable reverse phase column (50 mM ammoniumacetate pH 7.0; Column: VYDAC 228 TP, The Separations group, Hesperia, Calif., USA) on an HPLC instrument.

BRIEF DESCRIPTION OF THE DRAWING

As shown in FIG. 1, the purified PICP gives only one band in SDS-polyacrylamide gel electrophoresis and upon reduction produces only two bands with a molar ratio of about 2:1, indicating that the product is free of type III carboxyterminal propeptide.

EXAMPLE 2

Figure 1:
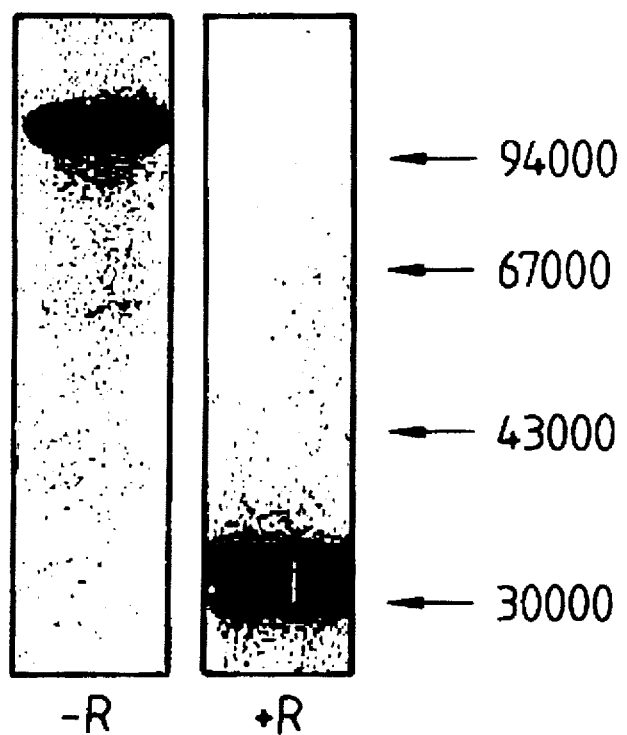
FIG. 1 shows the results of SDS-polyacrylamide gel electrophoresis of the purified PICP. In the figure the two runs shown are those of unreduced material (−R) and material which has been reduced with 2-mercaptoethanol (+R). The arrows indicate the positions of standard proteins: 94000 is phophorylase b, 67000 is bovine serum albumin, 43000 is ovalbumin and 30000 is carbonic anhydrase.

Performance of the equilibrium type of radioimmunoassay:

Ten micrograms of the carboxyterminal propeptide of type I procollagen are labelled with 1 millicurie of iodine 125 by chloramine-T (5 micrograms) and the labelled propeptide is separated from free iodine by gel filtration on a SEPHACRYL S-300 column (1×20 cm) equilibrated in PBS-buffer containing 1 mg/ml bovine serum albumin. The labelled propeptide (or tracer) is eluted from the column as a sharp peak well before free iodine. Callibration is carried out by establishing antiserum binding curves prepared with 50,000 radioactivity counts per minute of the labelled propeptide. The propeptide concentration in an unknown sample of serum or other body fluids is determined in the following radioimmuno inhibition assay: a pretested amount of the antiserum is incubated with the unknown sample and 50,000 counts per minute of the tracer for 2 hours at 37° C. Then a solid phase second antibody against rabbit gamma globulin is added and after 15 min incubation at 20° C. the antigen bound in the immune complex is separated by centrifugation from the solution. The inhibition activity of the unknown sample is compared with the activity of the standard concentrations of unlabelled type I procollagen carboxyterminal propeptide.

We claim:

1. A method for assaying carboxyterminal propeptide of human type I procollagen which comprises contacting in any order (i) a sample of a human body fluid selected from the group consisting of blood, plasma, and serum, which sample is obtained from a person known or suspected to be suffering from a metabolic bone disease or other disease affecting bones; (ii) an antibody which specifically binds to carboxyterminal propeptide of human type I procollagen but not human type III procollagen carboxyterminal propeptide, said antibody being capable of measuring quantitatively an amount of carboxyterminal propeptide of human type I procollagen of from 40 to 200 µg/l in human serum, and (iii) a label such that the label is bound in an amount which depends on the amount of propeptide present in the sample, and assaying the amount of the bound or unbound label as a measure of the level of carboxyterminal propeptide of human type I procollagen in the sample.

2. The method of claim 1 in which the sample is human serum.

3. A method according to claim 1 in which labelled carboxyterminal propeptide of type I procollagen and the sample to be assayed are contacted with the antibody, the propeptide-antibody complex so formed is separated from the uncomplexed material and the complexed or uncomplexed label is assayed.

4. A method according to claim 1 in which the label is radioactive, enzymatic, luminescent or fluorescent.

5. A method according to claim 1 in which the complex formed from said propeptide and said antibody, the first antibody, is contacted with a second antibody which is an antibody which specifically binds to the first antibody, and the propeptide-antibody-antibody complex is separated from the uncomplexed material.

6. A method according to claim 5 in which the second antibody is immobilized to a solid support.

7. A kit suitable for use in carrying out an assay method according to claim 1 comprising a first antibody which specifically binds to carboxyterminal propeptide of human type I procollagen but not human type III procollagen carboxyterminal propeptide, said antibody being capable of measuring quantitatively an amount of carboxyterminal propeptide of human type I procollagen of from 40 to 200 µg/l in human serum, a second antibody which is an antibody which specifically binds to the first antibody, a label, and a solid support to which is immobilized the first or second antibody.

8. A kit suitable for use in carrying out an assay method according to claim 1 comprising an antibody which specifically binds to carboxyterminal propeptide of human type I procollagen but not human type III procollagen carboxyterminal propeptide, said antibody being capable of measuring quantitatively an amount of carboxyterminal propeptide of human type Procollagen of from 40 to 200 µg/l inhuman serum, and a label.

* * * * *